Figures 1, 2:
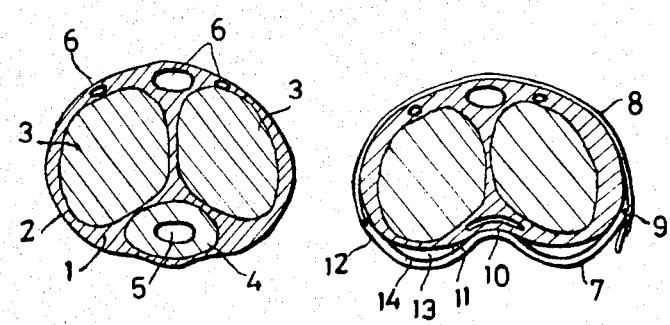

United States Patent [19]

de Leur et al.

[11] Patent Number: 4,534,353

[45] Date of Patent: Aug. 13, 1985

[54] ACCESSORY FOR COUNTERACTING THE CONSEQUENCES OF VESICAL INCONTINENCE WITH MALES

[76] Inventors: Eric J. A. de Leur, Sydwende 9, Drachten; Berend Heijenga, Schaapstreek 42, Sleen, both of Netherlands

[21] Appl. No.: 478,448

[22] Filed: Mar. 24, 1983

[30] Foreign Application Priority Data

Mar. 17, 1983 [NL] Netherlands ............... 8201258

[51] Int. Cl.³ .................................................. A61B 19/00
[52] U.S. Cl. ............................ 128/346; 128/DIG. 25; 251/9
[58] Field of Search ............ 128/346, 79, DIG. 25; 604/349, 250, 34; 251/4, 9

[56] References Cited

U.S. PATENT DOCUMENTS

| | | | |
|---|---|---|---|
| 261,354 | 7/1882 | Johnson | 251/9 |
| 678,943 | 7/1901 | Davis | 128/346 |
| 729,423 | 5/1903 | Scheiber et al. | 251/9 |
| 2,455,859 | 12/1948 | Foley | 128/346 |
| 2,533,924 | 12/1950 | Foley | 128/346 |
| 2,756,753 | 7/1956 | Means | 128/346 |
| 3,147,754 | 9/1964 | Koessler | 128/346 |
| 3,773,290 | 11/1973 | Mowery | 251/9 |
| 3,916,902 | 11/1975 | Lineberger | |
| 3,926,175 | 12/1975 | Allen et al. | 128/346 |
| 4,139,007 | 2/1979 | Diamond | 128/DIG. 25 |

FOREIGN PATENT DOCUMENTS

| | | |
|---|---|---|
| 336834 | 5/1920 | Fed. Rep. of Germany . |
| 2504301 | 8/1976 | Fed. Rep. of Germany . |
| 2545477 | 4/1977 | Fed. Rep. of Germany . |
| 2717924 | 10/1978 | Fed. Rep. of Germany . |
| 7902192 | 9/1979 | Netherlands . |
| 1019286 | 2/1966 | United Kingdom . |
| 2016929 | 10/1979 | United Kingdom . |
| 2036561 | 7/1980 | United Kingdom . |

*Primary Examiner*—C. Fred Rosenbaum
*Assistant Examiner*—Gene B. Kartchner
*Attorney, Agent, or Firm*—Daniel C. McKown

[57] ABSTRACT

An accessory for counteracting the consequences of vesical incontinency with males, comprising an annular tensioning means (8, 9) adapted to be tensioned around the penis (1) of the user, and further comprising a pressure element (7) with a rounded and relatively stiff pressing surface (10) having a curvature which is substantially adpated to the shape of the swelling bodies (3) of the penis (1) so as to pinch the urethra (5) elastically against said bodies (3) which are retained by the tensioning means (8, 9), said pressure element (7) being, in particular, a strip of a substantially rigid material having, more in particular, lateral portions (16, 17) which are substantially adapted to the shape of said bodies (3).

11 Claims, 4 Drawing Figures

U.S. Patent    Aug. 13, 1985    4,534,353

ACCESSORY FOR COUNTERACTING THE CONSEQUENCES OF VESICAL INCONTINENCE WITH MALES

Vesical incontinence is a rather frequently occurring ailment for which different causes exist, which can, in fact, all be reduced to an insufficient activity of the vesical sphincter. This is a very great inconvenience for a person suffering therefrom, which may, moreover, have very serious psychical consequences, e.g. when an incontinent person will isolate himself for shame.

For the purpose of counteracting this, various accessories have already been proposed, comprising either a collecting vessel or absorbing tissues. A collecting vessel is to be worn under the clothes, and is connected, by means of a thin hose, with a catheter, or, in the case of males, sometimes with a special condom provided with a hose connection. The absorbing tissues can be worn in different manners, depending on the degree of incontinency. In the case of so-called dripping incontinency with males, sometimes a condom filled with absorbing material will suffice, as described in Netherlands Pat. No. 79 02 192.

Such accessories are onerous. A collecting vessel impedes walking and/or sitting, and should be emptied in time. Absorbing tissues and the like are, in the wet condition, inconvenient, and are, moreover, to be replaced in time, so that the user should always have a sufficient supply thereof with him.

For males another solution has been proposed in W. Germany Pat. No. 2 717 924, in which, in fact, the operation of the sphincter is simulated. To that end use is made of a strap made of a soft fabric, which can be tightened around the penis, and an extension made of an unstretchable stiffer material can be closed around this strap by means of a barbed tape fastener to form a closed ring. In the tightened condition a small cushion provided on the inner side of the former strap will press against the urethra, which can be sufficiently constricted thereby for preventing a urine discharge. The advantage of the barbed tape fastener is that it can be quickly fastened and loosened, and is adjustable in arbitrary positions. However the pressure should not be so high that blood vessels would be throttled.

Now this known accessory has several draw-backs. The principal draw-back is that, in order to allow to constrict the urethra sufficiently, a high tension force is to be exerted by means of the strap. This can have as a consequence that the blood flow towards and from the surface tissues will become insufficient. Moreover the skin can be easily pressed into folds, which is onerous as well. An important practical objection is, moreover, that adjusting the tension is very difficult, since the strap is to be pulled through a slot before being fixed by means of the barbed tape fastener, which, because of the friction in said slot, impedes a quick loosening. The tightened strap prevents, moreover, a possible expansion of the penis during wearing which can lead to additional pinching effects.

There exists a great need for a good and easily manipulatable accessory for counteracting the consequences of vesical incontinency with males.

The accessory according to the invention comprises an annular tensioning means to be arranged around the penis of the user and provided, at its inner side, with a pressure element which is adapted, in the tightened condition of the tensioning means, to compress the urethra, said accessory being characterised in that the pressure element has a rounded and relatively rigid pressing surface, having a curvature which is substantially adapted to the shape of the swelling bodies situated at both sides of the urethra, all this in such a manner that the pressure surface, when tightening the tensioning means, can be pressed into the penis so as to press the urethra elastically against these swelling bodies, which bodies are laterally supported by the pressure surface, the tensioning means being adapted to maintain a substantially constant circumference of the penis.

The pressure surface should be so rigid that the elastic pressing force exerted on the urethra is mainly provided by the swelling bodies, which are restrained at the other side by the tensioning means. In this manner the urethra can be squeezed without a considerable tensioning force, and without undesired pinching effects occurring.

In particular the pressure element is formed by a strip of a substantially rigid material such as a plastic bent with the desired rounding. This strip can, in particular, be somewhat flexible at least at both sides of the pressure surface, and can have, at both sides of said pressure surface, a curvature which, at least partly, is adapted to the shape of the swelling bodies which are pressed aside somewhat by the pressing surface. If necessary said strip can be provided with one or more portions with a higher flexibility acting as elastic hinges.

Moreover the pressure element can be formed by or can be provided with a pressing piece, e.g. made of plastic, rubber or the like having a radius of curvature corresponding to the desired rounding, which pressing piece can have, in particular in the axial plane, an inwardly directed curvature, and can be rounded at its extremeties in order to avoid pinching phenomena near the lateral edges of the pressure surface.

The pressing element consists, preferably, of a strip which is divided by means of two sets of hinges, the inner hinges delimiting a pressing body, and the outer hinges being connected to a set of outer parts connected to the tensioning means, which pressing body engages a crank to be actuated by means of a lever, by means of which this body can be moved between a releasing position and a tensioning position, which crank can be locked in the tensioning position. In particular the pressing body is provided with a retracting portion surrounding the crank, in order to retract unambiguously said body when moving the actuating lever towards the releasing position.

In order to avoid pinching larger blood vessels situated near the surface of the penis, the inner side of the tensioning means is preferably provided with a cushion which is corrugated in such a manner that the pressing forces provided by the tensioning means are exerted on the penis outside the region of these blood vessels.

If, in the known manner, the tensioning means is a strap to be fixed by means of a tensioning buckle and connected to the pressure element, it can sometimes be advisable to provide the strap in a point corresponding to the highest admissible force with a stop means which cannot be pulled past the tensioning buckle.

It can sometimes be favourable to provide the tensioning means with one or more air cushions, inside which the pressure can be adjusted at will by means of a small pump and a pressure control valve, so as to be able to provide, in this manner, a continuously adjustable tensioning force.

It should be noted that, from U.S. Pat. No. 3,916,902, it is known to fix a collecting sleeve on the penis by means of an inflatable terminal rim, but then no closing of the urine discharge will occur. From W. Germany Pat. No. 2 504 301 it is known to constrict the urethra by means of a liquid bladder to be arranged inside the body, but this requires an often onerous operation.

The invention will be elucidated below in more detail by reference to a drawing, showing in:

FIG. 1 a simplified diagrammatic cross-section of a penis;

FIG. 2 a section corresponding to FIG. 1 with an accessory according to the invention in the operative condition shown in front view;

FIGS. 3A and B partial sections of a special embodiment of a part of the accessory according to the invention; and FIGS. 4A and B views, partly in section, of an other embodiment of the accessory according to the invention in the inoperative and operative conditions resp.

As diagrammatically shown in FIG. 1, a penis mainly consists of tissue 1 situated at the outer side with epidermis 2, within which two swelling bodies (corpora cavernosa) 3 and an intermediate spongy body (corpus spongiosum) 4 are present. In the latter body the urethra 5 is situated. Moreover blood vessels are present in the tissue 1, the major ones being shown at 6.

In FIG. 2 it is shown how, according to the invention, the urethra 5 is compressed. To that end a pressure element 7 is used, consisting of a strip of relatively rigid plastics connected to a tensioning strap 8, the latter being adapted to be tightened by means of an easily releasable fastener 9. This fastener can be of any suitable type, e.g. as known in braces, luggage straps, etc., and, if desired, also a barbed tape fastener can be used.

The strip 7 has a central bend 10 which, when tightening the strap 8, presses the penis slightly inwardly so that the spongy body 4 is pushed upwards. The urethra 5 is compressed and closed as shown, and is, then, stopped by the swelling bodies 8, and the latter can slightly be deformed thereby. The whole will behave more or less as a liquid mass which, conserving its volume as determined by the tensioning strap 8, remains deformable, but the tissues can be slightly elastically compressed. The bodies 3 apply themselves somewhat against lateral parts 11 of the bend 10, and also the terminal parts 12 of the strip 7 can provide support.

The tensioning strap 8 provides for maintaining a sufficient counter-pressure. The fastener 9 is adjusted in such a manner that the urethra 5 is completely closed by compression, but the blood flow through the blood vessels 6 is not impeded.

In order to allow for some swelling of the penis, use can be made of the flexibility of the strip 7, and the parts 12 can be made more flexible so that they will obtain, when being tightened, a corresponding curvature, and the interspaces 13 between the outer bends 14 of the strip 7 and/or the adjacent portion of the strap 8, on the one hand, and the epidermis 2, on the other hand, still allow for a local expansion of the penis, which, moreover, can be conducive to maintaining the blood flow in that portion.

The strip 7 can be manufactured in a number of different sizes, in order to allow for an adaptation to different penis dimensions. This can, for the rest, also be obtained by means of the flexibility in the parts 12. This flexibility can be enhanced by forming, in the strip 7, weakened portions acting as elastic hinges.

Figure 3:

Although the edges of the strip 7 are rounded, they can, nevertheless, be troublesome. Then it may be advisable to use, in the manner of FIG. 3, a strip 7' which is flatter in its central part, and to arrange, there, a pressing piece 15 which, as shown in FIG. 3B, is also curved in the axial plane, and, thus, provides a gradual transition towards the edges of the strip 7'. This pressing piece can, for example, be somewhat elastic, and, in particular, can be made hollow, and this piece can, for example, consist of a piece of rubber or plastic hose.

Figure 4:
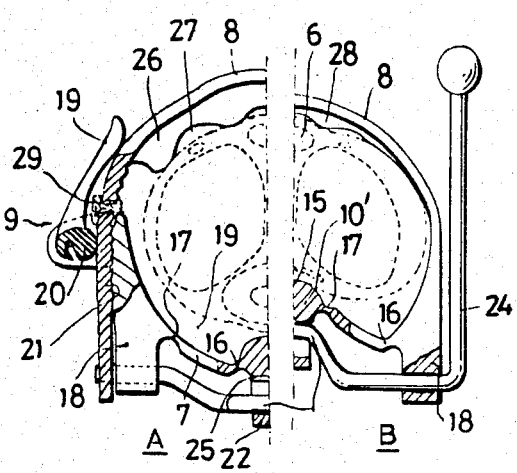

In FIG. 4 an embodiment of the accessory according to the invention is shown, which mainly comprises the same elements as the one of FIG. 2, which elements are indicated by the same reference numerals.

The pressing strip 7 is subdivided by means of two pairs of flexible hinges 16 and 17, the central part 10' serving as the pressing body proper, which can be provided with an arched pressure piece 15, the outer hinges 16 each being connected to a thicker outer part 18, one of which being connected to the tensioning strap 8, which in particular, can be extruded together therewith as one piece of plastics, the other outer part 18 being provided with the fastener 9. This fastener consists, in the case shown, of a lever 19 with an excenter roll 20 forming a unitary structure therewith, and being adapted to press the strap 8, which may be provided with corrugations 21 in that region, against the adjacent surface of the outer part 18, which surface can be provided with similar corrugations so that, then, the strap can be unambiguously clamped.

The central part 10' is, at its lower side, provided with an open hook 22. In the gap between this hook 22 and the lower surface of the central part 10' a crank 23 is arranged, having extremities which are rotatable supported in the lateral parts 18, and one extremity is extended by an actuating lever 24 for actuating the crank 23.

In the operative position of FIG. 4B the bend of the crank 23 engages with a recess 25 in the lower side of the central part 10', so that the crank will be retained in this position. If necessary additional locking means can be provided for retaining the lever 24. The hook 22 serves to take along the central part 10' downwards when rotating the crank 23 towards the position of FIG. 4A.

In order to avoid that the blood vessels 6 will be pinched, it can be favourable to provide a pressing cushion 26 which is provided with rounded recesses 27 in the neighbourhood of these blood vessels, the intermediate portions 28 then transmitting the pressure towards the penis outside the region of the blood vessels 6.

The fastener 9 is adjusted in such a manner that, in the position of FIG. 4B, the urethra is effectively constricted, but the blood circulation is not impeded. This adjustment can, for instance, be experimentally determined, after which the strap 8 can be marked accordingly. This can, in particular, be done as shown by pinching in a rivet 29 preventing that the strap 8 will be pulled past the adjusted position. It will be clear that also other manners of marking are possible.

Such an accessory can be manufactured from plastic in a simple manner, and in particular the flexible strip 7 with the hinges 16 and 17 and the terminal parts 18, as well as the strap 8, can be extruded as one single piece. The crank 23 with the actuating lever 24 can be made, for instance, of metal wire, and can be snapped into suitable keyhole-shaped recesses of the lateral parts 18.

The fastener 9 can be hooked or snapped on a pin formed on the lateral piece 18. In this manner the accessory can be quickly assembled, which will have a favourable influence on the retail price. Moreover such an accessory can be easily cleaned.

When using the embodiment of FIG. 2, the strap 8 is tightened to such an extent that the urethra is squeezed, and to bring about a urine discharge, the buckle or fastener 9 is to be loosened. Thereafter the strap 8 is tightened again. When using the embodiment of FIG. 4, the accessory is positioned on the penis with the crank in the position of FIG. 4A; thereafter the strap 8 is pulled through until the marking 29 has reached the fastener 9, and then the strap is fixed by means of said fastener. Subsequently the lever 24 can be shifted towards the position of FIG. 4B for squeezing the urethra. For bringing about a urine discharge, only the lever 24 has to be switched again, so that the central part 10' is moved downwards, and the urethra is opened thereby. At the end of the urine discharge, the lever 24 is returned towards the position of FIG. 4B. The fastener 9 is only to be actuated for removing the accessory from the penis.

Instead of the above-mentioned means for squeezing the urethra, also inflatable air cushions can be used by means of which the tensioning force can be adjusted at will by pumping in air, e.g. by means of a rubber ball, and by discharging the air by means of an adjustable valve. These air cushions can be provided under the central part 10 or 10' or at the location of the pressing cushion 26. The operation of such an accessory does not differ from that of the embodiment described above. When using an air cushion, the releasable fastener 9 can sometimes be left out, and a local compression for avoiding the pinching of blood vessels can be obtained by a suitable design of the air cushion, or by subdividing said cushion into partial cushions.

Within the scope of the invention many modifications are possible.

It can, sometimes, be sufficient to use simple pressing cushions 26 made of a foam material without the rounded recesses 27.

A fundamental requirement is that the urethra is sufficiently compressed for preventing any urine discharge. The swelling bodies 3 are relatively hard, and the force exerted by the strip 7, and in particular the bend or rounding 10 thereof, should not be higher than required for compressing the spongy body 4, and thereby the urethra 5. Moreover the shape of the rounding 10 should be adapted to the shape of the swelling bodies 3 in such a manner that the urethra 5 will be kept centered between said bodies. If the central part 10 is too steep, it is possible that the urethra 5 will slide away laterally, and then the compression thereof will be insufficient. In fact the elastic compression of the spongy body 4 will be sufficient for closing the urethra, and thus too high pressures in other parts of the penis, and in particular in the blood vessels, will be avoided.

We claim:

1. A pressure element for use in an applicance for counteracting the consequences of vesical incontinence in males, said pressure element applied in use to the underside of the penis and held thereto by a tensioning band that extends circumferentially around the penis, said pressure element comprising:

a first rigid member located to the right of the urethra;

a second rigid member located to the left of the urethra;

a pressing body located between said first rigid member and said second rigid member and including a convex pressing surface that faces the urethra for applying a radially inward force to the underside of the penis for compressing the urethra;

connecting means interconnecting said pressing body with said first rigid member and with said second rigid member and including surfaces of concave shape that face and cradle the corporae cavernosa, whereby the pressing surface is maintained in alignment with and overlying the urethra; and, actuating means mounted to said first rigid member and mounted to said second rigid member and operatively engaging said pressing body for forcing said pressing body against the urethra under control of the user.

2. The pressure element of claim 1 wherein said first rigid member, said second rigid member, said pressing body, and said connecting means are parts of a unitary structure.

3. The pressure element of claim 1 wherein said connecting means further comprise strips of a stiff material.

4. The pressure element of claim 3 wherein said strips include spaced portions that are more flexible than the remainder of said strips.

5. The pressure element of claim 4 wherein said spaced portions are of reduced thickness, whereby said spaced portions are more flexible and act as hinges.

6. The pressure element of claim 3 wherein each of said strips includes spaced hinges to impart flexibility to each of said strips.

7. A pressure element for use in an applicance for counteracting the consequence of vesical incontinence in males, said pressure element applied in use to the underside of the penis and held thereto by a tensioning band that extends circumferentially around the penis, said pressure element comprising:

a first rigid member located to the right of the urethra;

a second rigid member located to the left of the urethra;

a pressing body located between said first rigid member and said second rigid member and including a convex pressing surface that faces the urethra for applying a radially inward force to the underside of the penis for compressing the urethra;

connecting means interconnecting said pressing body with said first rigid member and with said second rigid member and including surfaces of concave shape that face and cradle the corporae cavernosa, whereby the pressing surface is maintained in alignment with and overlying the urethra; and, crank means mounted to said first rigid member and mounted to said second rigid member and operatively engaging said pressing body for forcing said pressing body against the urethra under control of the user.

8. The pressure element of claim 7 further comprising a lever connected to said crank means for use by the user in operating said crank means.

9. The pressure element of claim 8 further comprising locking means for retaining said lever in a locked position.

10. The pressure element of claim 9 wherein said locking means is shaped to allow quick release of said lever from the locked position.

11. The pressure element of claim 7 wherein said pressing body further includes an open hook portion that pivotably engages said crank means.

* * * * *